April 4, 1967 A. P. HOWARD Plant Pat. 2,730
ROSE PLANT
Filed Feb. 1, 1966
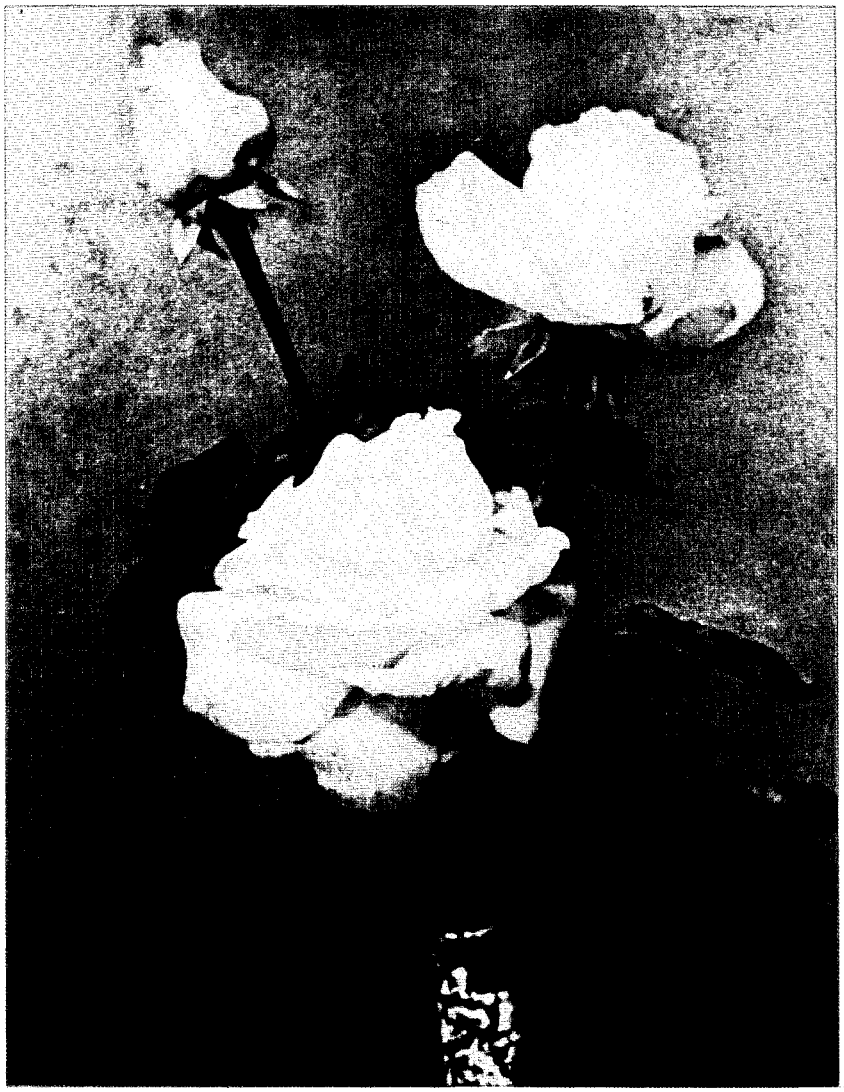
INVENTOR.
ARTHUR P. HOWARD
BY J. F. Cuneo
ATTORNEY United States Patent Office Plant Pat. 2,730
Patented Apr. 4, 1967

2,730
ROSE PLANT

Arthur P. Howard, Sierra Madre, Calif., assignor to Great Western Rose Company, Inc., Pomona, Calif., a corporation of California Filed Feb. 1, 1966, Ser. No. 526,960
1 Claim. (Cl. Plt.—18)

This invention relates to a new and distinct variety of rose plant that is ordinarily classified as a hybrid tea rose.

The plant resulted from cross-breeding of Contrast, an unpatented rose, with Queen Elizabeth, a patented rose bearing United States Plant Patent No. 1,259, after numerous experiments conducted by me at Montebello, California. The original plant was produced by me in 1955, using Contrast as the seed parent and Queen Elizabeth as the pollen parent.

The flowers produced by the new variety of rose plant are pink, and when the buds are fully opened form a medium sized bloom that is borne at the end of a medium length stem and somewhat resembled a camellia in the way the petals are arranged. The flowers are produced in abundance during the growing season that extends from February through November in the coastal region of Southern California. The plant forms a large, well branched upright bush and has a profusion of leaves.

In comparing the blooms of my new variety with those of its seed parent, Contrast, the flowers are a French Rose, whereas those of the seed parent are a rosy pink with a silver reverse. Compared to its pollen parent Queen Elizabeth, the pale pink flowers differ considerably from the flowers of the pollen parent in that those of the pollen parent are a carmine rose. The leaves of the new variety are much larger than the leaves of the pollen parent in that they are considerably larger and more luxuriant in growth. The plant is very hardy, exhibiting a vigorous upright habit, some of the plants have been known to reach a height of six feet.

The new rose belongs to the outdoor bush type and is used primarily for garden ornamentation. The plant has been reproduced asexually by budding performed in Montebello, California. The plant and flowers resulting, have reproduced true with all of the distinguishing characteristics being transmitted through the succeeding propagations of the variety; the plant cannot be reproduced true from seed.

The accompanying illustrations in full color show a typical specimen of buds and a partially opened flower with foliage, as well as a fully opened bloom. The colors are as true as it is possible to reproduce them by this type of color reproduction.

A detailed description of the new variety of rose follows, and to facilitate identification of the important colors described in this specification, the designations adopted by the British Horticultural Colour Charts have been followed.

The new rose belongs to the outdoor bush type and is of the so-called hybrid tea class. Its beautiful pale pink moderate-sized blooms surrounded by the luxuriant growth of leaves that are quite large for this type of rose make it particularly desirable for garden ormamentation as well as for cut flowers.

*The flower*

Locality where grown and observed: Montebello, California; Los Angeles, California; and West Los Angeles, California.

Flowers borne: The flowers are borne usually as single flowers on medium length stems that vary from ten to fifteen inches in length.

Number of blooms: When grown outdoors the plant produces an abundance of flowers, there being as many as fifty blooms on the plant at one time.

Continuity: The plant blooms continually from late February through the month of November. The plant does not seem to be particularly affected by hot or cold weather.

Fragrance: This variety has a very noticeable sweet fragrance that is delicate.

Bud:

*Peduncle.*—Length: Varies from two and one-half to three and one-half inches. Color: Brownish-green.

*Before calyx breaks.*—Size: About one and one-quarter inches in length and three-quarters of an inch in diameter. Form: The bud is ovoid with the upper end sharp-pointed.

*As calyx breaks.*—Color: French Rose 520. Sepals: Shape—Spear shaped with an almost parallel broad base. Size—Approximately three-eighths of an inch in width and three-quarters of an inch in length.

*As first petal opens.*—Size: One and one-quarter inches in length and about one and one-quarter inches in width. The petals are reflexed particularly at the upper margin. Color: Inside—The color is French Rose 520. Underside—The underside of the petals varies from French Rose 520/1 to French Rose 520/3, as the base is approached. Form: Substantially round with a retuse margin, the notch located near the center of each petal. Opening: Opening is low, the flower retaining a high center like a camellia and eventually becoming cup shaped as the petals roll outwardly.

Bloom:

*Size.*—Flowers are from three to four inches in diameter.

*Petalage.*—Number of petals varies from thirty to thirty-five.

*Form.*—Globular to cup shaped, with the inner petals slightly smaller than the outer petals.

*Petals.*—Shape: The petals are substantially round with the upper margin retuse, the notch in each petal being substantially near the upper central point. Size: The fully matured petals are approximately one and three-quarters inches long and one and three-quarters inches wide. Color: Upper side—the upper side of the petals is French Rose 520. Under side—the underside of each petal is French Rose 520/1 at the outer margin and gradually shades to French Rose 520/3 as the base is approached. Texture: The petals are rather thick but soft, the outer portion of the petal being more satiny than the inner portion.

*General color effect.*—The general overall color effect is French Rose 520.

*Behaviour.*—Petals drop off fairly clean. The flowers are not appreciably affected by hot weather.

*Flower longevity.*—The flowers last from five to eight days on the plant and have approximately the same longevity when they have been cut.

*Reproductive organs*

Stamens: Average in number, could be classed as medium.

Filaments: Filaments are about three-eights of an inch in length.

*Color.*—Filaments are substantially white.

Anthers: Anthers are not prominent. Color: Yellow.

Pollen:

*Quantity.*—Rather sparse.

*Color.*—Golden yellow.

Pistils: Few.
Styles: Not too prominent. Size and arrangement: The styles are very short and are bunched.
Stigma: Color: Greenish.
Ovaries: Ovaries are enclosed in calyx.
Hips:
*Length.*—About one-half inch in length and three-eighths of an inch wide.
*Form.*—Oblong.
*Color.*—Green with a slight russet tinge.
Seeds: None have been observed.

*The plant*

Foliage: Compound, odd pinnate leaves having an average of five leaflets.
*Quantity.*—Heavy.
*Leaflets.*—Shape: Best described as ovate with the tip cuspidate, having a slightly cordate base; margin serrulate. Size: The leaflets are up to two and three-quarters inches long and one and three-quarters inches wide. Color: Top—Parsley Green 00962. Underside—Willow Green 000862/2.
*Young Leaflets.*—Color: Upper—Reddish-green. Underside—Greenish-red.
*Type.*—Imparipinnate.
Stipules: Not too flaring and short.
Growth: Habit and height—Very vigorous, upright and well branched. Plant grows from five to six feet in height. The plant has very good productivity.
Canes: The diameter of the canes varies from three-quarters to one inch in diameter.

Main stems:
*Length.*—Four to six feet.
*Color.*—Light to medium green.
*Prickles (large).*—Size and number: There are very few prickles and what do appear are quite small.
*Prickles (large).*—The plant has so few of these that the number could be classed as none.
Branches:
*Color.*—Bright green.
*Shape.*—Predominantly vertical.
*Hair.*—None.
*Thorns.*—Number and size: Thorns are numerous. They are irregularly spaced on the branch and vary from one-quarter to five-sixteenths of an inch in length.
*New Shoots.*—Color: Bronzy red. Large and small prickles: None.

Having described my invention, I claim:

The new and distinct variety of rose plant of the class designated as hybrid tea roses, substantially as herein shown and described, characterized particularly as to novelty by the globular, medium-sized French Rose blooms borne as single flowers on medium length stems, the delicate, sweet fragrance of the flowers, the longevity of the flowers after they have been cut, the small number of prickles, the vigorous, tall upright growth habit of the plant, and the abundance of large sized leaflets.

No references cited.

ABRAHAM G. STONE, *Primary Examiner.*

ROBERT E. BAGWILL, *Examiner.*